(12) United States Patent
Liang et al.

(10) Patent No.: US 12,053,147 B2
(45) Date of Patent: Aug. 6, 2024

(54) MULTI-FIELD MINIATURIZED MICRO-ENDOSCOPE

(71) Applicant: Arizona Board of Regents on Behalf of the University of Arizona, Tucson, AZ (US)

(72) Inventors: Rongguang Liang, Tucson, AZ (US); Haijiang Cai, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 1371 days.

(21) Appl. No.: 16/222,921

(22) Filed: Dec. 17, 2018

(65) Prior Publication Data

US 2019/0209015 A1     Jul. 11, 2019

Related U.S. Application Data

(60) Provisional application No. 62/607,217, filed on Dec. 18, 2017.

(51) Int. Cl.
*A61B 1/00* (2006.01)
*A61B 1/04* (2006.01)
(Continued)

(52) U.S. Cl.
CPC .... *A61B 1/000096* (2022.02); *A61B 1/00117* (2013.01); *A61B 1/00167* (2013.01);
(Continued)

(58) Field of Classification Search
CPC ............ A61B 1/000096; A61B 90/361; A61B 1/00117; A61B 1/00167; A61B 1/0017;
(Continued)

(56) References Cited

U.S. PATENT DOCUMENTS 5,253,312 A * 10/1993 Payne .................... A61B 18/22
                                                    385/38
5,792,051 A * 8/1998 Chance .............. A61B 5/14546
                                                    600/476
(Continued)

FOREIGN PATENT DOCUMENTS

WO      2017079688      5/2017

OTHER PUBLICATIONS

Nieman LT et al. Compact beveled fiber optic probe design for enhanced depth discrimination in epithelial tissues. Opt Express. Feb. 16, 2009;17(4):2780-96 (Year: 2009).*

(Continued)

*Primary Examiner* — Ashley K Buran
*Assistant Examiner* — Helene Bor
(74) *Attorney, Agent, or Firm* — Perkins Coie LLP (57) ABSTRACT

A low-cost, ultra-compact multichannel micro-endoscope system is described that includes fiber bundles that can be implanted directly into the target tissue. In one example, the system includes one or more fiber bundles, where a first end of one fiber bundle is shaped as a non-flat surface for insertion into a target, allowing direct contact with a region of interest within the target. The light that travels back from varying depths of the region of interest are received at second end of the fiber bundle, is captured and the corresponding signals are processed to produce high-resolution images of the region of interest. Multiple imaging probes can be implanted into the target to simultaneously monitor neural activities in different regions and at different depths.

12 Claims, 8 Drawing Sheets

(51) Int. Cl.
  *A61B 1/045* (2006.01)
  *A61B 1/06* (2006.01)
  *A61B 1/07* (2006.01)
  *A61B 5/00* (2006.01)
  *A61B 90/00* (2016.01)
  *G02B 21/02* (2006.01)
  *G02B 21/36* (2006.01)
  *G02B 23/26* (2006.01)

(52) U.S. Cl.
  CPC ............ *A61B 1/0017* (2013.01); *A61B 1/042* (2013.01); *A61B 1/043* (2013.01); *A61B 1/045* (2013.01); *A61B 1/0646* (2013.01); *A61B 1/07* (2013.01); *A61B 5/0084* (2013.01); *A61B 5/7267* (2013.01); *A61B 90/361* (2016.02); *G02B 21/02* (2013.01); *G02B 21/361* (2013.01); *G02B 23/26* (2013.01); *A61B 2090/3614* (2016.02); *A61B 2090/367* (2016.02)

(58) Field of Classification Search
  CPC ......... A61B 1/042; A61B 1/043; A61B 1/045; A61B 1/0646; A61B 1/07; A61B 5/0084; A61B 5/7267; A61B 2090/3614; A61B 2090/367; A61B 2562/0242; G02B 21/02; G02B 21/361; G02B 23/26
  See application file for complete search history.

(56) References Cited

U.S. PATENT DOCUMENTS

| | | | |
|---|---|---|---|
| 5,842,995 A * | 12/1998 | Mahadevan-Jansen | A61B 5/4331 600/476 |
| 5,953,477 A * | 9/1999 | Wach | G02B 6/4203 385/115 |
| 6,002,480 A * | 12/1999 | Izatt | G01B 9/02072 356/479 |
| 6,016,376 A * | 1/2000 | Ghaemi | B82Y 35/00 385/12 |
| 6,038,360 A * | 3/2000 | Sugawara | G02B 6/06 385/116 |
| 7,006,741 B1 | 2/2006 | Yu | |
| 7,492,998 B2 | 2/2009 | Miller et al. | |
| 7,801,405 B2 * | 9/2010 | Daum | G02B 6/4298 385/115 |
| 8,385,695 B2 | 2/2013 | Li et al. | |
| 8,773,760 B2 | 7/2014 | Gmitro et al. | |
| 8,885,975 B2 * | 11/2014 | Yu | G06T 11/006 382/131 |
| 9,730,586 B2 | 8/2017 | Boularot et al. | |
| 2006/0155348 A1 * | 7/2006 | deCharms | A61N 5/0622 607/89 |
| 2015/0168702 A1 * | 6/2015 | Harris | G02B 21/367 250/306 |
| 2015/0309295 A1 | 10/2015 | Cocker et al. | |
| 2017/0199364 A1 | 7/2017 | Doric et al. | |
| 2017/0199369 A1 | 7/2017 | Doric et al. | |
| 2018/0364158 A1 * | 12/2018 | Wang | G01J 3/10 |

OTHER PUBLICATIONS

Glozman et al., "Framework for shape analysis of white matter fiber bundles". Neuroimage, 167 (2018), pp. 466-477 (Year: 2018).*
Ghosh, K. K. et al., Miniaturized integration of a fluorescence microscope, Nat. Methods, 2011, pp. 871-878, 8(10).
Ziv, Y. et al., Miniature microscopes for large-scale imaging of neuronal activity in freely behaving rodents, Curr. Opin. Neurobiol., 2015, pp. 141-147, 32.
Zong, W. et al., Fast high-resolution miniature two-photon microscopy for brain imaging in freely behaving mice, Nat. Methods, 2017, pp. 713-719, 14(7).
Huang, Y. et al., Design and research on miniature fluorescent microscope device, IEEE 10th Conference on Industrial Electronics and Applications (ICIEA), IEEE, 2015, pp. 483-488.
Byars J. L., et al., Development of an optrode for intramural multisite optical recordings of Vm in the heart, J. Cardiovasc. Electrophysiol., Nov. 2003, pp. 1196-1202, 14(11).
Kong, W. et al., A New Optrode Design for Intramural Optical Recordings, IEEE Trans Biomed Eng. Author manuscript, Nov. 2011, pp. 3130-3134, 58(11).
Doric Lenses, available at http://doriclenses.com/.
Gulati, S. et al., Video Article: Multi-Layer Cortical Ca2+ Imaging in Freely Moving Mice with Prism Probes and Miniaturized Fluorescence Microscopy, J. Vis. Exp., https://www.jove.com/video/55579, 2017.
Hooks, D.A. et al., Intramural Multisite Recording of Transmembrane Potential in the Heart, Biophysical J., Nov. 2001, pp. 2671-2680, 81.
Inscopix: Miniature Microscope Solutions for Circuit Neuroscience, available at https://www.inscopix.com/.
Silva, A. J., Miniaturized two-photon microscope: seeing clearer and deeper into the brain, Light: Science & Applications, 2017.

* cited by examiner

Top View

Side View

┌─────────────────────────────────────────────────────────┐
│ Provide light to a flat end of a fiber bundle in a      │
│ microscope, where the fiber bundle has another end that │
│ is shaped to include a smooth, non-flat surface, and    │
│ the fiber bundle includes a plurality of individual     │
│ optical fiber bundles                                   │
│ 802                                                     │
└─────────────────────────────────────────────────────────┘
                            │
                            ▼
┌─────────────────────────────────────────────────────────┐
│ Allow the light to propagate through the fiber bundle   │
│ to the smooth non-flat surface                          │
│ 804                                                     │
└─────────────────────────────────────────────────────────┘
                            │
                            ▼
┌─────────────────────────────────────────────────────────┐
│ Receive by the smooth, non-flat surface of the fiber    │
│ bundle light that is emitted or reflected from varying  │
│ depths of a region of interest in a target that is      │
│ illuminated by the light that exits the fiber bundle    │
│ through the smooth, non-flat surface thereof            │
│ 806                                                     │
└─────────────────────────────────────────────────────────┘
                            │
                            ▼
┌─────────────────────────────────────────────────────────┐
│ Process the received emitted light to produce a         │
│ high-resolution image or a group of images of the       │
│ region of interest                                      │
│ 808                                                     │
└─────────────────────────────────────────────────────────┘
```

FIG. 8

MULTI-FIELD MINIATURIZED MICRO-ENDOSCOPE

CROSS REFERENCE TO RELATED APPLICATIONS

This application claims priority to the provisional application with Ser. No. 62/607,217, titled "Multi-Field Miniaturized Micro-Endoscope," filed Dec. 18, 2017. The entire contents of the above noted provisional application are incorporated by reference as part of the disclosure of this document.

TECHNICAL FIELD

The technology in this patent document generally relates to imaging systems, and in particular to imaging systems that use fiber bundles for producing high-resolution images.

BACKGROUND

This section is intended to provide a background or context to the disclosed embodiments. The description herein may include concepts that could be pursued, but are not necessarily ones that have been previously conceived or pursued. Therefore, unless otherwise indicated herein, what is described in this section is not prior art to the description and claims in this application and is not admitted to be prior art by inclusion in this section.

In vivo electrophysiological recording has contributed significantly to the understanding of brain functions. Recent advances have enabled large-scale recordings of neural ensembles in a 3-D pattern in various brain regions. However, only a small subset of neurons can usually be recorded by electrophysiological recording. The spatial/anatomical organization of the neurons are usually unknown, leading to significant challenges in determining the identity of the neurons recorded.

Imaging techniques such as integrated miniature micro-endoscopes have been used to monitor neural activity in behaving animals. The existing micro-endoscope designs usually entail a flat surface gradient-refractive-index (GRIN) lens, which requires the attachment of a microscope baseplate docking system and other integrated components (light source, fluorescence filters, imaging optics, and a sensor) to the subject, such as a mouse's head. This configuration suffers from many shortcomings. For example, the micro-endoscope can be used in one brain region per animal, and is only capable of monitoring neural activity at a single depth. Hence, the neural activity at the different depths or across different brain regions cannot be obtained at the same time with the existing micro-endoscopes. Some techniques use a glass fiber bundle to provide illumination to the GRIN lens and to relay the image from the GRIN lens to the imaging system. With fiber bundle to relay the image, only the GRIN lens remains in the mouse's brain. In this technique, it is possible to implant more than one GRIN lens in the mouse's brain, but it is difficult to attach more than one glass fiber bundles to the mouse's head because, among other reasons, the glass fiber bundle is not flexible enough for a moving subject (such as a mouse) and more space is needed to attach fiber bundles to the GRIN lenses, thereby limiting the number of GRIN lenses which can be implanted.

Moreover, such systems require a GRIN lens, which can increase the cost and the number of components of the endoscopic system. The use of a GRIN lens further makes the existing systems unsuitable for obtaining 3D images because the GRIN lens can only obtain a plane image at its focal plane. The disclosed embodiments, among other benefits and features, address the above noted issues and describe compact, low-cost and versatile imaging devices and associated methods that can facilitate acquisition and processing of images obtained from biological tissues and other objects of interest.

DETAILED DESCRIPTION

In the following description, the word "exemplary" is used to mean serving as an example, instance, or illustration. Any embodiment or design described herein as "exemplary" is not necessarily to be construed as preferred or advantageous over other embodiments or designs. Rather, use of the word exemplary is intended to present concepts in a concrete manner.

As noted earlier, the existing imaging systems with applications in biological and in vivo imaging often include a GRIN lens, which in addition to being expensive and bulky, can only obtain a plane image at its focal plane and is thus not suitable for producing 3D images of the target tissue. The disclosed embodiments overcome these and other shortcomings of the existing systems by providing a low-cost, ultra-compact multichannel 3-D micro-endoscope system that relies on fiber bundles that can be implanted directly into the target tissue (such as a mouse's brain) without requiring a GRIN lens. In some embodiments, multiple imaging probes are implanted into the target to simultaneously monitor neural activities in different regions and at different depths.

Figure 1:
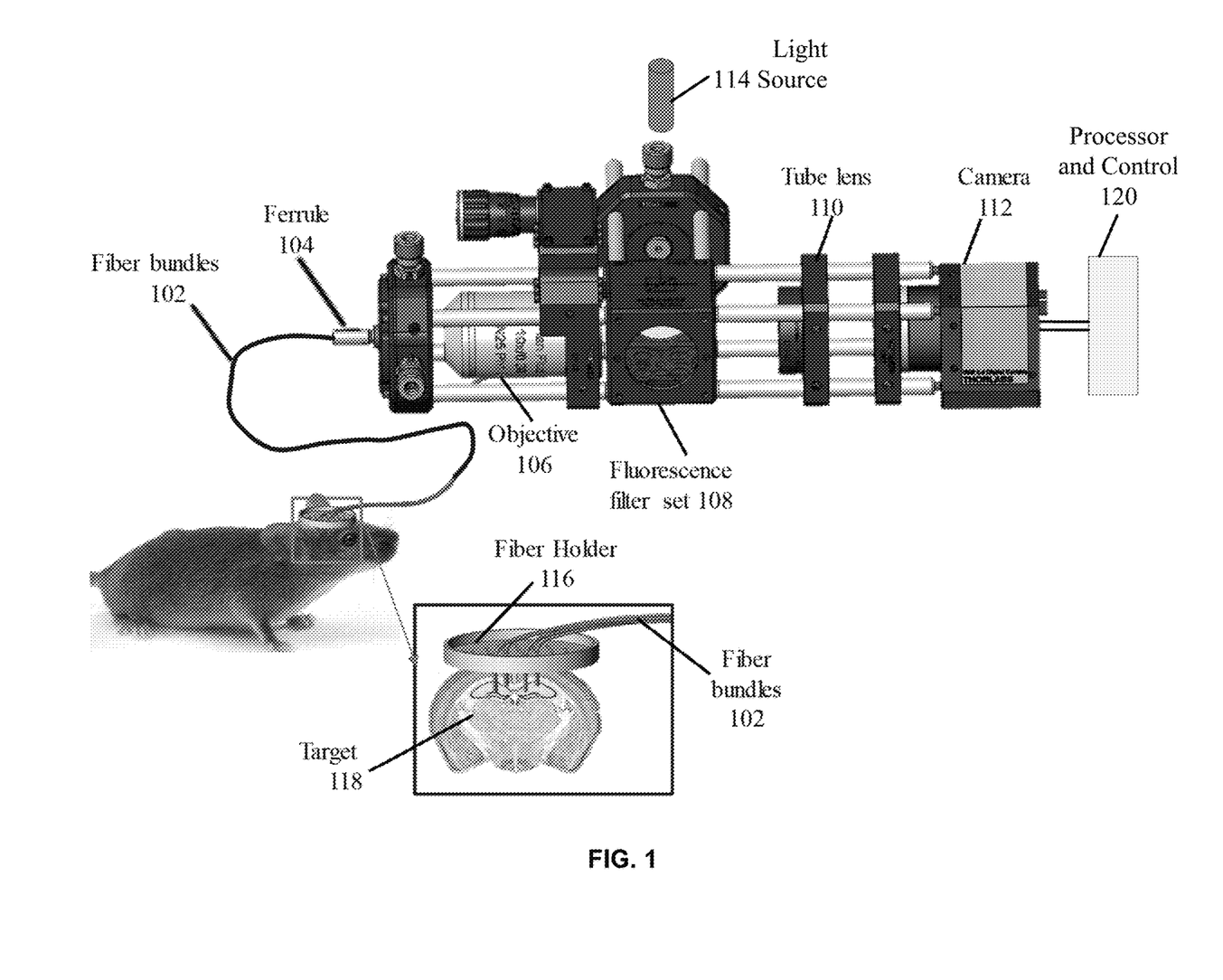
FIG. 1 illustrates an endoscopic system in accordance with an exemplary embodiment.

FIG. 1 illustrates an endoscopic system in accordance with an exemplary embodiment. The system includes a light source 114, a high-speed camera 112, a set of fluorescence filters 108, a microscope objective 106, a ferrule 104, a tube lens 110, and a number of flexible plastic fiber bundles 102. Each fiber bundle is, and operates as, an implantable imaging probe. One end of each fiber bundle can pass through a fiber holder 116 and implanted in the target 118; each fiber bundle can be implanted in a particular region of interest within the target 118. The non-implantable ends of the fiber bundles 102 can be glued together and polished to a flat surface. The excitation light from the light source 114 is coupled to the fiber bundles 102 through the objective lens 106. The light travels down the fiber bundles and excites the fluorescence at different regions of the target. The collected fluorescence light from different regions are received by the fibers in the fiber bundles 102 and imaged simultaneously onto the camera's sensor by the objective lens 104 and the tube lens 110. The received signals associated with the images are processed by the processor and control 120 components (e.g., a laptop, a microprocessor and memory, a mobile device and the like).

In the configuration of FIG. 1, the plastic fiber bundle with, for example, a diameter less than 0.5 mm, is mounted on the animal's head, providing a very lightweight (e.g., 0.3 g/m) and flexible arrangement that makes it feasible to implant a number of polymer fiber bundles into the subject's brain, which in turn allows simultaneous monitoring of the neural activity at different regions. The fiber holder allows the fiber bundles to be wrapped and fitted into a small package that is placed on, for example, the mouse's head. One example of the fiber bundle is MBI-450S from Asahi Kasei Corporation, which has 7,300 fibers and in which the distance between fiber core is 5 μm. The features include low price, excellent flexibility, and little fracture, resulting in easy fabrication and ease of connectivity with other parts, as compared with a glass fiber. In some embodiments, the diameter of each fiber is in the range 2 μm to 10 μm.

Figure 2:
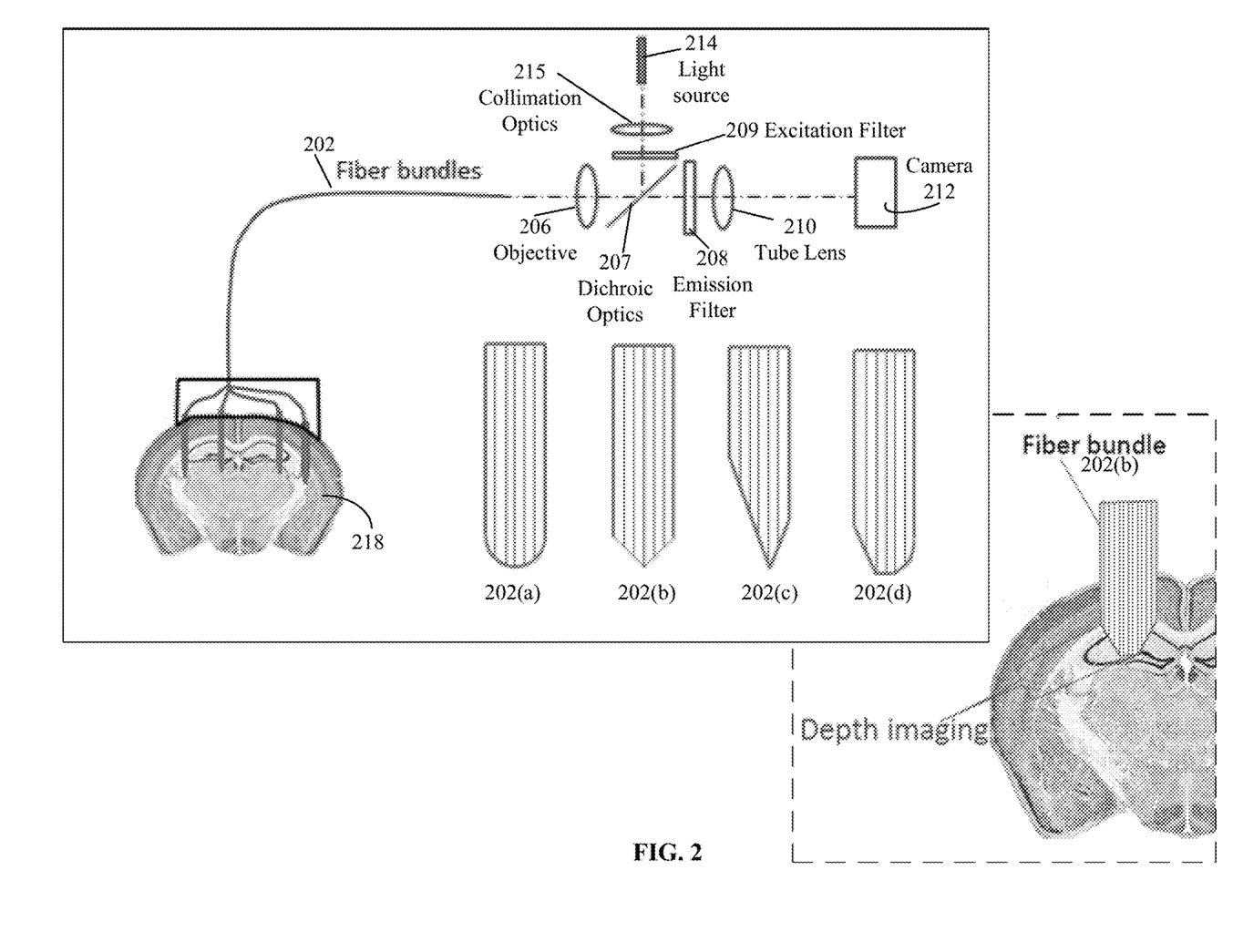
FIG. 2 illustrates an endoscopic system having a plurality of fiber bundles with differing end profiles in accordance with an exemplary embodiment.

The disclosed configuration further allows imaging of a region at different depths by customizing the contact surface of the fiber bundle to various shapes. FIG. 2 illustrates an endoscopic system that is adapted to use a plurality of fiber bundles with differing end profiles in accordance with an exemplary embodiment. In particular, the endoscopic system includes fiber bundles 202 that can be inserted into the region of interest in the target 218, a light source 214 and associated collimation optics 215, an excitation filter 209 an emission filter 208, dichroic optics 207, an objective lens 206, a tube lens 210 and a camera 212. The endoscopic system is adapted to include one or more fiber bundles 202, having particular end profiles, as represented by the four exemplary end profiles 202(a) through 202(d). Each fiber bundle having, for example, one of end profiles 202(a) through 202(d), can be used to capture images at different depths and different directions from the same region of the target 218.

The inset of FIG. 2 shows fiber bundle 202(b) that is inserted into a region of the brain tissue, which allows light from different depths to be captured in accordance with the angled profile of the fiber end. In some embodiments, the fiber bundle is shaped to include an end profile that is customized to a particular target geometry of interest. For example, a region of interest of the brain can be mapped to identify the shape of the regions of neural activity (e.g., via dissection, or via imaging techniques). The mapping can then be used to form a particular end profile for a fiber bundle that matches the identified region in order to enable imaging of the regions of neural activity that occur at different depths. In this way, the fiber end (or a portion thereof) can be shaped as a continuous and smooth non-flat surface that, when implanted into the subject, makes proper contact with the region of interest. As shown in FIG. 2, the non-flat surface at the end of each fiber bundle can form a non-orthogonal angle with respect to the optical axis of the fiber bundle (i.e., the axis that run along the length of the fiber bundle). Thus, the non-flat surface can form a plane that is at an angle with respect to a cross-sectional plane of the fiber bundle. For example, the non-flat surface can be a surface that forms a non-orthogonal angle with respect to an optical axis of the at least one fiber bundle, a surface that has a linear surface profile, or a surface that has a non-linear surface profile.

Figure 3:
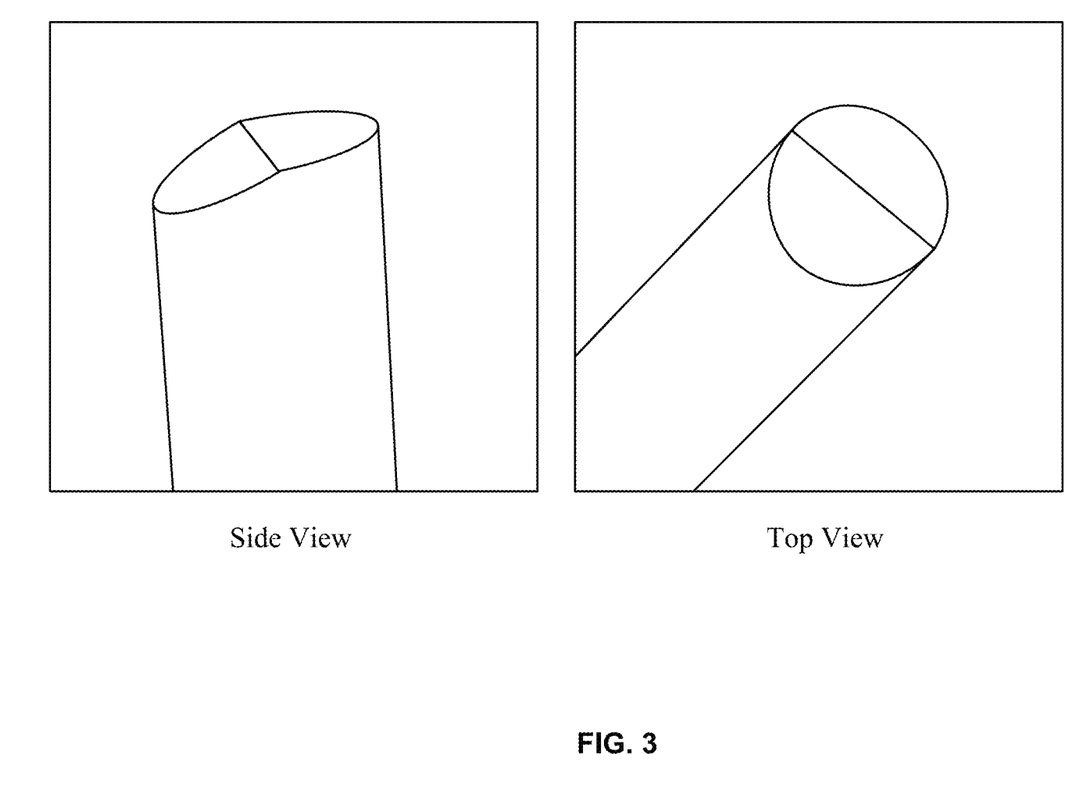
FIG. 3 illustrates a side view and a top view of a custom fiber bundle end in accordance with an exemplary embodiment.

It should be noted that the four end profiles 202(a) through 202(d) only illustrate a few examples of many possible profiles that can be implemented in accordance with the disclosed technology. Moreover, it is understood that while the depicted fiber ends are shown as having two-dimensional profiles, the end profiles are generally three-dimensional. FIG. 3 shows a side view and a top view of one example custom fiber bundle end that is cut with an angle with respect to a flat surface.

The microscope configurations that are shown in FIGS. 1 and 2 are especially suited for fluorescence microscopy. That is, the target is illuminated with light of a specific wavelength (or wavelengths) which is absorbed by the tissue that is treated, died or stained with the proper material that absorb the incoming light, and emit light at a different wavelength (or wavelengths). The illumination light is separated from the emitted fluorescence through the use of a spectral emission filter (see, e.g., element 208 in FIG. 2). The filters and the dichroic beamsplitter (see, e.g., element 209 in FIG. 2) are chosen to match the spectral excitation and emission characteristics of the material that is used to treat the tissue. It should be noted, however, that at least some of the disclosed technology can be used with other types of microscopes.

Figure 4:
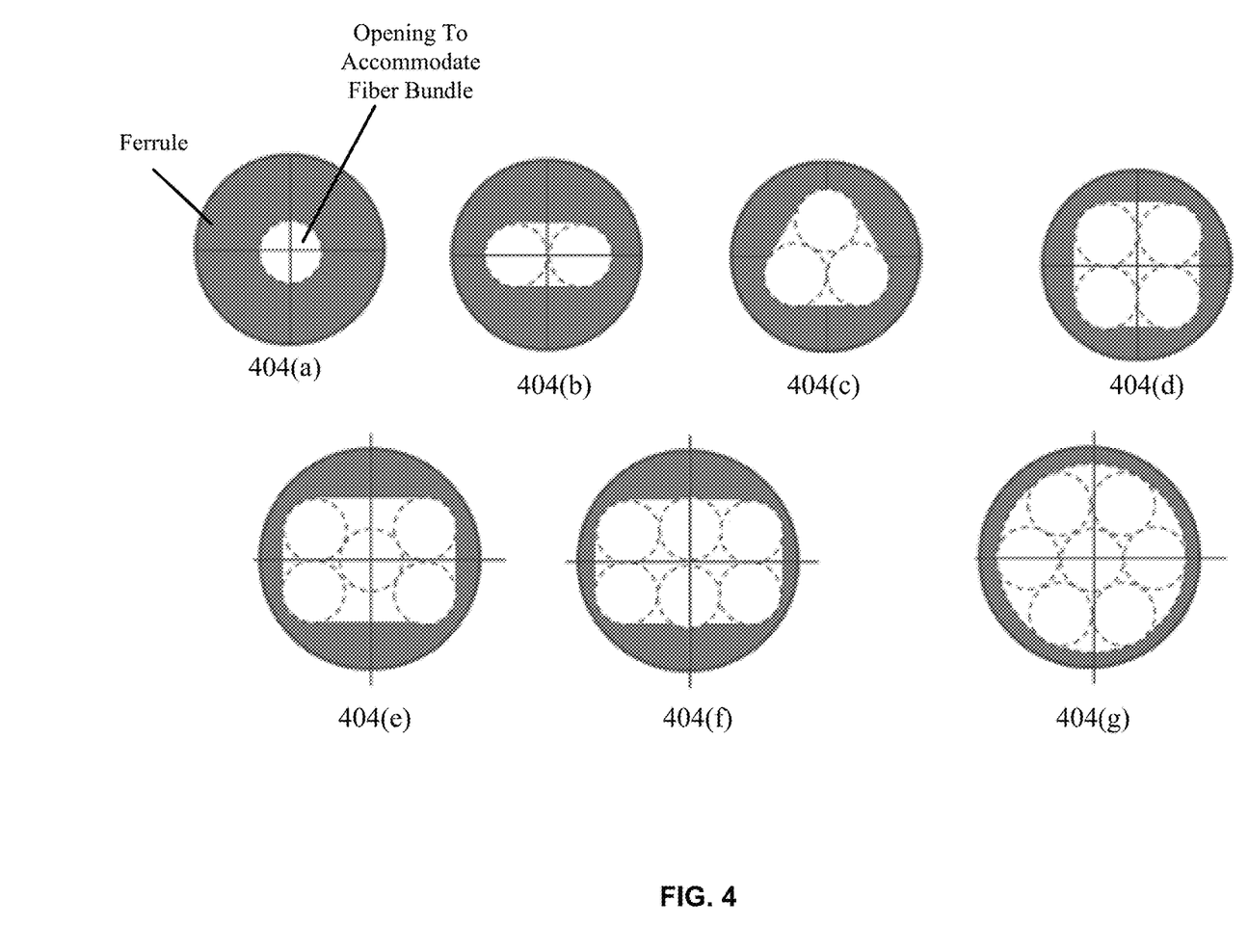
FIG. 4 illustrates different ferrules that can accommodate different numbers of the fiber bundles in accordance with exemplary embodiments.

In order to assemble the fiber bundles together, a ferrule is typically used. As illustrated in FIG. 1, the ferrule 104 is positioned at the non-implantable end of the fibers. FIG. 4 illustrates examples of different ferrules that can be used to hold different number of the fiber bundles in configurations 404(a) through 404(g). By the way of example and not by limitation, configurations 404(a) through 404(g) illustrate ferrules that are configured to accommodate one of the following number of fiber bundles to pass therethrough: one fiber bundle, two fiber bundles, three fiber bundles, four fiber bundles, five fiber bundles, six fiber bundles, or seven fiber bundles. After the fiber bundles are assembled onto the ferrule, the end of all fiber bundles can be cut to produce a flat end which allows excitation light to be uniformly coupled into all fiber bundles and the images to be accurately imaged onto the sensor.

Figure 5:
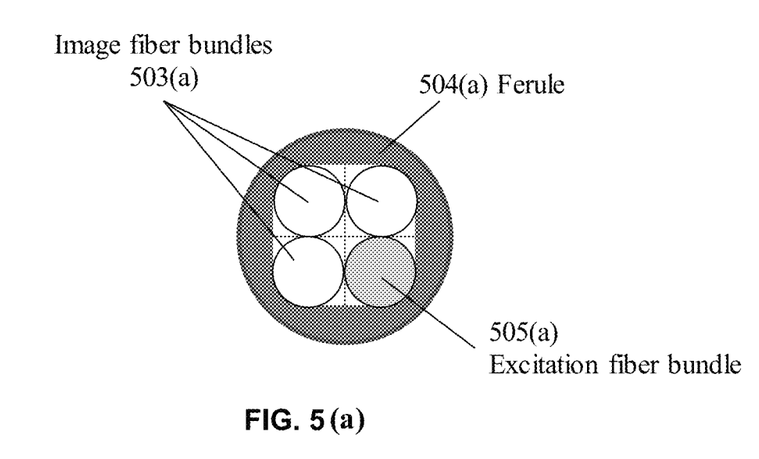
FIG. 5(a) illustrates a fiber bundle configuration to facilitate illumination and imaging in accordance with an exemplary embodiment.
FIG. 5(b) illustrates another fiber bundle configuration to facilitate illumination and imaging in accordance with an exemplary embodiment.
FIG. 5(c) illustrates another fiber bundle configuration to facilitate illumination and imaging in accordance with an exemplary embodiment.

In accordance with some embodiments, neural activity can be stimulated in one or more regions through one or more fiber bundles, while allowing neural activities in other regions to be captured through the other fiber bundles. In some embodiments, all fiber bundles may be used to provide excitation illumination, while all but one of the fiber bundles is used to detect the emitted light. In such configurations, the fiber bundle that is exclusively used to provide excitation can augment, or provide a further control mechanism, for providing light excitation. FIG. 5(a) illustrates one example of a ferule 504(a) that accommodates four fiber bundles in a configuration that utilizes one fiber bundle 505 for excitation, and three fiber bundles 503 for imaging purposes. This configuration allows simultaneous (or near simultaneous) excitation in one region and imaging of the neural activity in different regions using the same low-cost equipment. In one example implementation, the excitation regions are controlled by a spatial light modulator, such as a digital micromirror device (DMD).

In some embodiments, one or more fibers within a fiber bundle (instead of the entire fiber bundle) are used to provide excitation light to stimulate small regions. Typically a projection system with spatial light modulator, such as liquid crystal device (LCD), liquid crystal on silicon (LCoS), and TI's digital micromirror device (DMD), is used to project the patterns on the fiber bundles through the microscope objective. Some example configurations are shown in FIGS. 5(b) and 5(c), where the dark-colored fibers illustrate the fibers that are used to provide excitation to very small regions on the target. In particular, in FIG. 5(b), a ferule 504(b) accommodates four fiber bundles in a configuration that utilizes three sections 505(b) of one fiber bundle for excitation, and the remaining sections of that fiber bundle and three other fiber bundles 503(b) for imaging purposes. In FIG. 5(c), a ferule 504(c) accommodates four fiber bundles in a configuration that utilizes a plurality of sections 505(c) of three fiber bundles for excitation, and the remaining sections of those fiber bundles and one other fiber bundle 503(c) for imaging purposes. It should be noted that other variations of the above configurations (e.g., including fewer or additional fiber bundles and/or subsections thereof) can be used to provide different excitation and imaging patterns.

Figure 6:
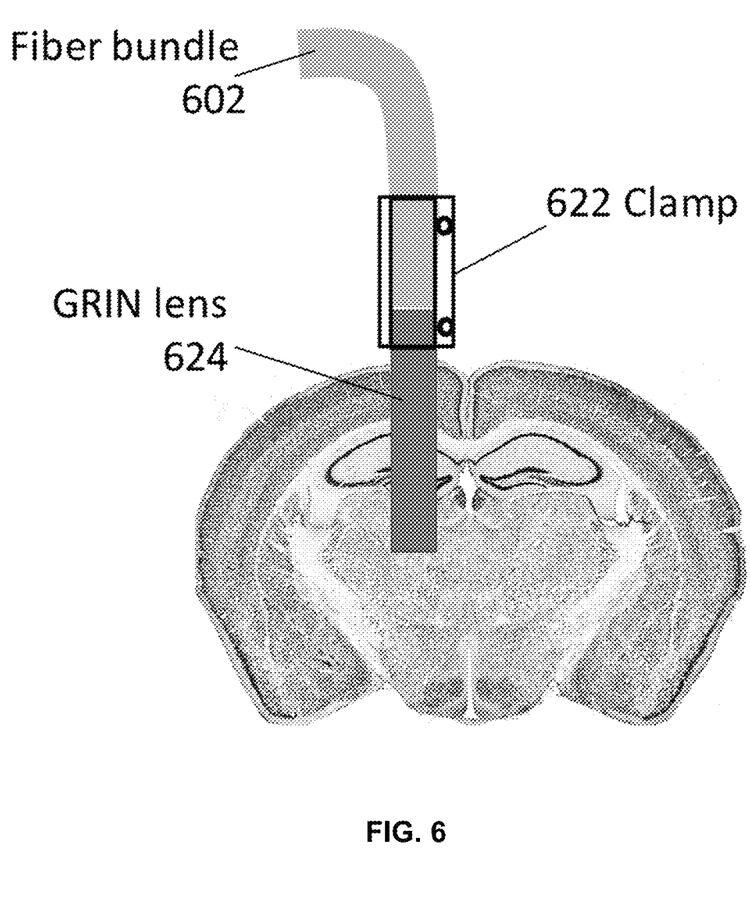
FIG. 6 illustrates an endoscope configuration that includes plastic fiber bundle with two flat ends connected to an implanted GRIN lens in accordance with an exemplary embodiment.

While the above described embodiments eliminate the need for implanting a lens into the target volume, the use of the disclosed plastic fibers can be incorporated into systems that use an implantable lens, as well. One such system is illustrated in FIG. 6, where a plastic fiber bundle 602 with two flat ends is connected to an implanted GRIN lens 624 through a compact clamp 622. Since the plastic fiber bundle is very flexible, it is suitable for multi-region imaging.

The disclosed embodiments can be particularly advantageous for implementation in endoscopes that provide high resolution images. Such images can be obtained by bundling thousands of small-diameter fibers that are closely packed in a bundle. The camera sensor can detect the light from each of the fibers, and based on the detected light, provide the corresponding electronic signals to the processor. Such signals are received and processed by a processor (e.g., a microprocessor) for presentation on a screen or a display device, or for storage as image/video files. The image processing operations carried out by the processor can vary depending on several factors including the extent of image distortion (e.g., caused by the movement of the subject under test), the cost or computational capabilities of the processing components, the needed resolution of the images, and the like.

Figure 7:
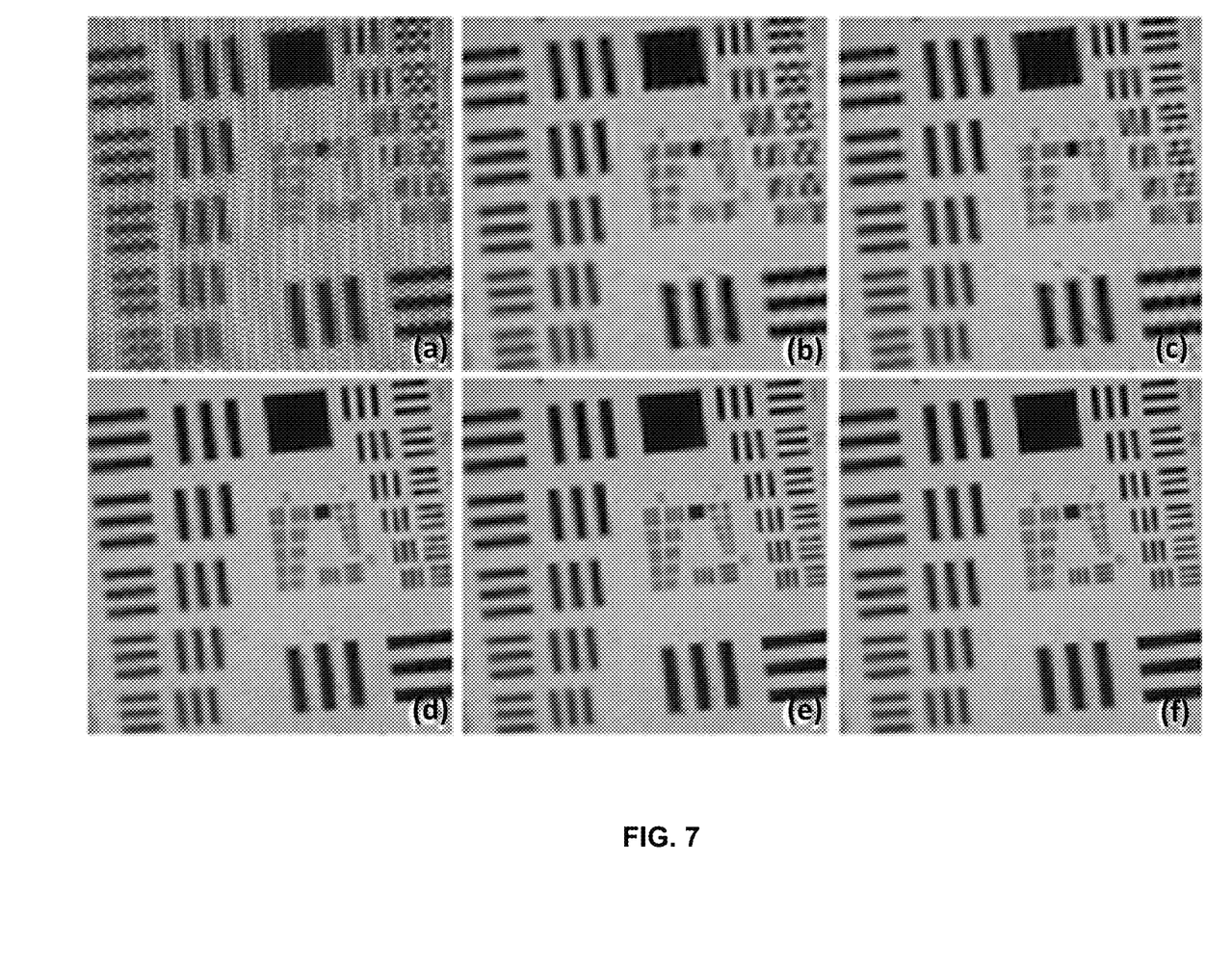
FIG. 7 illustrates a series of images that are produced through capture and processing of signals obtained by an endoscope in accordance with some exemplary embodiments.

In some implementations, the image processing operations include removing the artifacts due to the fiber configurations. FIG. 7 illustrates a series of images that are produced through capture and processing of signals obtained by an endoscope in accordance with some exemplary embodiments. For example, as shown in image (a) of FIG. 7, a honeycomb pattern may be present in the image captured by the camera. In image (b), the honeycomb pattern is removed by, for example, identifying the honeycomb (dark) pixels, and replacing the honeycomb pixel values with the extrapolated values from a plurality of neighboring pixels. In some embodiments, image artifacts (e.g., random noise, motion artifacts, etc.) can be removed by computing an average (e.g., a weighted average) of the pixel values over a sequence of images that are captured in close temporal proximity of one another. For example, images (b) through (f) in FIG. 7 illustrate images that are obtained based on processing 1, 2, 4, 8 and 16 images, respectively. Motion estimation and compensation techniques can further be used in processing images from a moving target. One approach is to use the forward model to map a high-resolution representation to multiple images modeling random probe motions. The forward model computes a maximum a posteriori (MAP) estimate of the high-resolution image from one or more low-resolution images using conjugate gradient descent. Another approach is to use deep learning-based restoration methods, such as a generative adversarial restoration neural network, to remove honeycomb patterns and improve spatial resolution. The brightness mapping should be constructed in the training neural network so that the trained network can have the ability to output images of the expected brightness.

Figure 8:
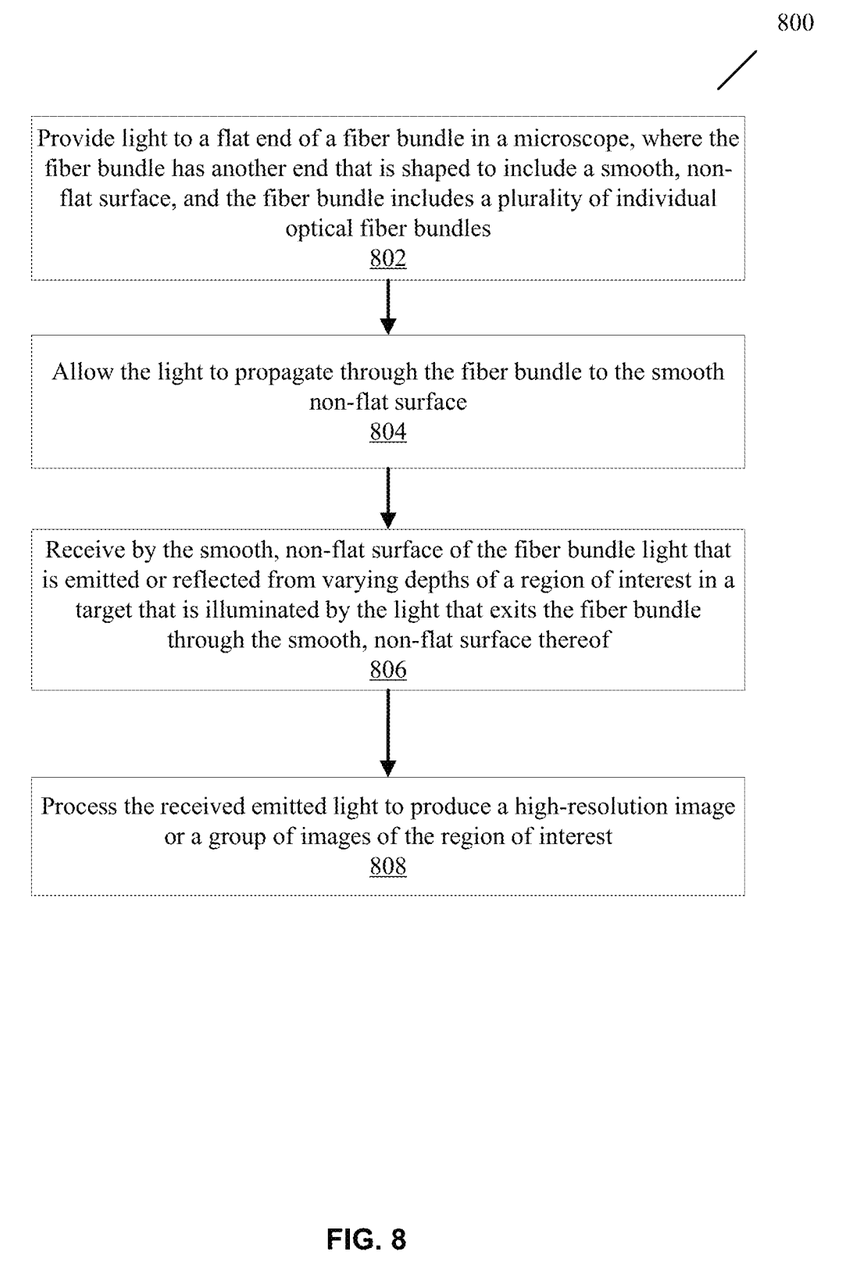
FIG. 8 illustrates a set of operations that can be carried out to produce a high-resolution image in a microscope in accordance with an exemplary embodiment.

FIG. 8 illustrates a set of operations 800 that can be carried out to produce a high-resolution image in a microscope in accordance with an exemplary embodiment. At 802, light is provided to a flat end of a fiber bundle in a microscope. The fiber bundle has another end that is shaped to include a smooth, non-flat surface, and the fiber bundle includes a plurality of individual optical fiber. At 804, light is allowed propagate through the fiber bundle to the smooth non-flat surface. At 806, light that is emitted or reflected from varying depths of a region of interest in a target is received. The light is received by the smooth, non-flat surface of the fiber bundle when the region of interest is illuminated by the light that exits the fiber bundle through the smooth, non-flat surface thereof. At 808, the received emitted light is processed to produce a high-resolution image or a group of images of the region of interest.

In one example embodiment, the above operations further include using the high-resolution images or the group of images to simultaneously monitor neural activities in different regions and at different depths. In another example embodiment, providing light to a flat end of a fiber bundle includes providing excitation light to a first subset of the plurality of individual optical fibers, and receiving the light that is emitted or reflected from varying depths of a region of interest includes receiving the light from a second subset of the plurality of individual optical fibers. In yet another exemplary embodiment, processing of the received light to produce the images includes removing an imaging artifact due to a configuration of individual fibers within the fiber bundle. For example, the imaging artifact can include a honeycomb pattern. In still another exemplary embodiment, the processing includes producing a plurality of images that are captured in close temporal proximity of one another.

One aspect of the disclosed embodiments relates to an imaging system for use in a microscope that includes a light source, and one or more flexible fiber bundles, where each fiber bundle includes a plurality of individual fibers. A first end of at least one fiber bundle is shaped to include a non-flat surface for insertion into a target, and is shaped to directly contact a region of interest within the target. The imaging system also includes a microscope objective positioned to receive light from the light source and to couple the light to a second end of at least one fiber bundle. The microscope objective is further configured to receive emitted or reflected light from the region of interest that propagates through differing lengths of optical fibers of one or more of the fiber bundles. The imaging system additionally includes a sensor positioned to receive the emitted or reflected light after propagation through the differing lengths of optical fibers within the at least one fiber bundle to enable formation of an image of the region of interest having varying depths.

In one exemplary embodiment, all fiber bundles have a flat surface at their respective second ends. At another exemplary embodiment, second ends of all fiber bundles collectively form a flat surface that is positioned to receive the light from the microscope objective at a substantially orthogonal angle. In yet another exemplary embodiment, the first end of the at least one fiber bundle has a shape that matches a surface of the region of interest. In one exemplary embodiment, the one or more fiber bundles include plastic fibers. In another exemplary embodiment, at least one of the one or more flexible fiber bundles includes at least one thousand individual optical fibers. In still another exemplary embodiment, the plurality of individual fibers includes fibers having a diameter in the range 2 µm to 10 µm.

According to another exemplary embodiment, the imaging system also includes a ferrule including a hollow center to allow the one or more flexible fiber bundles to pass therethrough. In one exemplary embodiment, the imaging system includes at least two fiber bundles, where the first end of a first fiber bundle is shaped for insertion into a first region of interest within the target and the first end of a second fiber bundle is shaped for insertion into a second region of interest within the target. In another exemplary embodiment, where the imaging system includes at least two fiber bundles, a first fiber bundle is configured to deliver light to a first region of interest within the target, and a second fiber bundle is configured to receive emitted or reflected light from a second region of interest within the target. In one exemplary embodiment, the second fiber bundle is also configured to deliver light to the second region of interest.

In one exemplary embodiment, one or more individual fibers within the one or more flexible fiber bundles is configured to deliver light to the region of interest. In another exemplary embodiment, the imaging system further includes an excitation filter positioned between the light source and the microscope objective to provide excitation light having a first wavelength or range of wavelength to the region of interest, and an emission filter positioned between the microscope objective and the sensor to only allow emitted light having a second wavelength or range of wavelengths to reach the sensor.

In some exemplary embodiments, the imaging system further includes a processor coupled to the sensor and a memory comprising processor executable code. The processor executable code when executed by a processor configures the processor to receive image data from the sensor and to process the image data. In one exemplary embodiment, the processor executable code when executed by a processor configures the processor to process the received image data to remove an imaging artifact due to a configuration of individual fibers within at least one of the one or more flexible fiber bundles. For example, the imaging artifact includes a honeycomb pattern. In another exemplary embodiment, the processor executable code when executed by a processor configures the processor to process a plurality of images that are captured in close temporal proximity of one another to produce an output image. In still another exemplary embodiment, the processor executable code when executed by a processor configures the processor to produce a sequence of moving images representative of images captures within a particular period of time. According to another exemplary embodiment, the first end of at least one of the one or more flexible fiber bundles forms an irregularly-shaped non-flat surface.

Another aspect of the disclosed embodiments relates to an image capture device for use in a microscope that includes one or more flexible fiber bundles, where each fiber bundle includes a plurality of individual optical fibers. Additionally, a first end of at least one fiber bundle is shaped as a non-flat surface for insertion into a target, the non-flat surface is shaped to directly contact a region of interest within the target, and the non-flat surface allows light from the region of interest to travel through a length of the at least one fiber bundle from varying depths of the region of interest at the first end of the fiber bundle to a second end of the fiber bundle. The image capture device also includes a lens positioned to receive the light after the light has traveled through the length of the at least one fiber bundle to enable formation of a 3-dimensional image of the region of interest corresponding to the varying depths of the region of interest.

It is understood that the various disclosed embodiments may be implemented individually, or collectively, in devices comprised of various hardware and/or software modules and components. These devices, for example, may comprise a processor, a memory unit, an interface that are communicatively connected to each other, and may range from desktop and/or laptop computers, to mobile devices and the like. The processor and/or controller can be in communication with at least one memory and with at least one communication unit that enables the exchange of data and information, directly or indirectly, through the communication link with other entities, devices and networks. The communication unit may provide wired and/or wireless communication capabilities in accordance with one or more communication protocols, and therefore it may comprise the proper transmitter/receiver antennas, circuitry and ports, as well as the encoding/decoding capabilities that may be necessary for proper transmission and/or reception of data and other information.

Some of the disclosed devices or modules can be implemented as hardware, software, or combinations thereof. For example, a hardware implementation of electronic devices can include discrete analog and/or digital components that are, for example, integrated as part of a printed circuit board. Alternatively, or additionally, the disclosed components or modules can be implemented as an Application Specific Integrated Circuit (ASIC) and/or as a Field Programmable Gate Array (FPGA) device. Some implementations may additionally or alternatively include a digital signal processor (DSP) that is a specialized microprocessor with an architecture optimized for the operational needs of digital signal processing associated with the disclosed functionalities of this application. Similarly, the various components or sub-components within each module may be implemented in software, hardware or firmware. The connectivity between the modules and/or components within the modules may be provided using any one of the connectivity methods and media that is known in the art, including, but not limited to, communications over the Internet, wired, or wireless networks using the appropriate protocols.

Various information and data processing operations described herein are described in the general context of methods or processes, which may be implemented in one embodiment by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), etc. Therefore, the computer-readable media that is described in the present application comprises non-transitory storage media. Generally, program modules may include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps or processes.

The foregoing description of embodiments has been presented for purposes of illustration and description. The foregoing description is not intended to be exhaustive or to limit embodiments of the present invention to the precise form disclosed, and modifications and variations are possible in light of the above teachings or may be acquired from practice of various embodiments. The embodiments discussed herein were chosen and described in order to explain the principles and the nature of various embodiments and its practical application to enable one skilled in the art to utilize the present invention in various embodiments and with various modifications as are suited to the particular use contemplated. The features of the embodiments described herein may be combined in all possible combinations of methods, apparatus, modules, systems, and computer program products.

What is claimed is:

1. A method for producing a high-resolution image in a microscope, comprising:
   mapping a region of interest of a target to obtain a shape of a region of interest within the target;
   providing light to a flat end of a fiber bundle in the microscope, the fiber bundle having another end that is shaped to include a non-flat end surface, wherein the fiber bundle includes a plurality of individual optical fibers, and is selected such that the non-flat end surface of the fiber bundle matches the shape of the region of interest;
   allowing the light to propagate through the fiber bundle to the non-flat end surface;
   receiving by the non-flat end surface of the fiber bundle light that is emitted or reflected from varying depths of the region of interest in the target that is illuminated by the light that exits the fiber bundle through the non-flat end surface thereof; and
   processing the received emitted light to produce the high-resolution image or a group of images of the region of interest.

2. The method of claim 1, further comprising using the high-resolution images or the group of images to simultaneously monitor neural activities in different regions and at different depths.

3. The method of claim 1, wherein:
   providing light to a flat end of a fiber bundle includes providing excitation light to a first subset of the plurality of individual optical fibers; and
   receiving the light that is emitted or reflected from varying depths of the region of interest includes receiving the light from a second subset of the plurality of individual optical fibers.

4. The method of claim 1, wherein the processing comprises removing an imaging artifact due to a configuration of individual fibers within the fiber bundle.

5. The method of claim 4, wherein the imaging artifact includes a honeycomb pattern.

6. The method of claim 1, wherein the processing comprises producing the group of images that are captured in close temporal proximity of one another.

7. The method of claim 1, wherein the processing comprises producing a sequence of moving images representative of images captured within a particular period of time.

8. The method of claim 1, wherein:
   prior to providing the light to the flat end of the fiber bundle, using an excitation filter to provide the light within a first wavelength or range of wavelengths; and
   processing the received emitted light includes processing the received emitted light after passing through an emission filter that only allows passage of light having a second wavelength or range of wavelengths.

9. The method of claim 1, wherein the processing comprises using a trained neural network to produce the high-resolution image.

10. The method of claim 1, wherein the processing comprises using a forward model to compute a maximum a posteriori (MAP) estimate of the high-resolution image from one or more low-resolution images using conjugate gradient descent.

11. The method of claim 1, wherein the processing includes removing an imaging artifact that is a motion artifact.

12. The method of claim 1, wherein the processing includes producing a three-dimensional (3D) image of the region of interest.

* * * * *